United States Patent
Ditzel et al.

(10) Patent No.: US 8,586,778 B2
(45) Date of Patent: Nov. 19, 2013

(54) CARBONYLATION PROCESS

(75) Inventors: Evert Jan Ditzel, East Yorkshire (GB); Bogdan Costin Gagea, Hull (GB)

(73) Assignee: BP Chemicals Limited, Middlesex (GB)

( * ) Notice: Subject to any disclaimer, the term of this patent is extended or adjusted under 35 U.S.C. 154(b) by 134 days.

(21) Appl. No.: 13/138,990

(22) PCT Filed: May 6, 2010

(86) PCT No.: PCT/GB2010/000893
§ 371 (c)(1),
(2), (4) Date: Jan. 13, 2012

(87) PCT Pub. No.: WO2010/130971
PCT Pub. Date: Nov. 18, 2010

(65) Prior Publication Data
US 2012/0101298 A1    Apr. 26, 2012

(30) Foreign Application Priority Data
May 14, 2009 (EP) ...................................... 09251312

(51) Int. Cl.
*C07C 67/36* (2006.01)

(52) U.S. Cl.
USPC ............................................. 560/206; 560/1

(58) Field of Classification Search
CPC ........ C07C 67/38; C07C 51/14; C07C 67/08; C07C 69/75; C07C 2101/14; B01J 2531/847
USPC ........................................................ 560/206, 1
See application file for complete search history.

(56) References Cited

U.S. PATENT DOCUMENTS

| | | | |
|---|---|---|---|
| 3,374,182 | A | 3/1968 | Young et al. |
| 5,118,482 | A | 6/1992 | Narayana et al. |

FOREIGN PATENT DOCUMENTS

| | | |
|---|---|---|
| DE | 41 16 630 A1 | 11/1992 |
| EP | 1 985 362 A1 | 10/2008 |
| WO | WO 2008/147190 A1 | 12/2008 |

OTHER PUBLICATIONS

PCT International Preliminary Report on Patentability; International Application No. PCT/GB2010/000893; filed May 6, 2010 (7 pgs).

*Primary Examiner* — Wu-Cheng Winston Shen
*Assistant Examiner* — Blaine G Doletski
(74) *Attorney, Agent, or Firm* — Nixon & Vanderhye

(57) ABSTRACT

A process for the production of acetic acid and/or methyl acetate by carbonylating methanol and/or reactive derivatives thereof with carbon monoxide in the presence of a catalyst which is a mordenite which has been treated with an aqueous basic solution containing at least one of aluminate ions and gallate ions and has a silica:$X_2O_3$ molar ratio (wherein X is Al and/or Ga) of at least 12:1.

14 Claims, No Drawings

CARBONYLATION PROCESS

This application is the U.S. national phase of International Application No. PCT/GB2010/000893 filed 6 May 2010 which designated the U.S. and claims priority to European Application No. 09251312.6 filed 14 May 2009, the entire contents of each of which are hereby incorporated by reference.

This invention relates to a carbonylation process for the carbonylation of methanol and/or reactive derivatives thereof with carbon monoxide to produce acetic acid and/or methyl acetate in the presence of a mordenite catalyst having improved carbonylation catalytic activity.

Zeolites are microporous crystalline structures that are widely applied as catalysts in the petroleum and chemical industries. Transport of molecules through zeolitic micropores occurs by diffusion and is believed to affect the rate of a reaction. However, the microporous network limits diffusion, hindering access to the active sites and limiting the reaction rate. Attempts have been made to improve catalytic effectiveness by the introduction of mesoporosity into the micropore structure. Mesopores provide improved access to the micropores thereby enhancing the rate of diffusion and thus the catalytic performance.

The selective extraction of silicon from a zeolite framework, referred to in the art as desilication, has proven to be an effective method of increasing mesoporosity in zeolites. The extraction of silicon from the framework will lead to a decrease in the silica:alumina molar ratio in the resulting zeolite.

Increasing the mesoporosity of mordenite by desilication is, for example, described in WO 2008/147190. In WO 2008/147190, a mesoporous mordenite is prepared by subjecting a non-dealuminated mordenite having an atomic ratio of framework Si to Al of at least 15, to an alkaline treatment, such as sodium hydroxide, in order to create mesoporosity by removal of silicon.

U.S. Pat. No. 5,118,482 describes a process for realuminating zeolites, thereby reducing their silica alumina ratio whereby the framework aluminium content of a framework deficient zeolite containing non-framework aluminium is increased by contacting the zeolite with an aqueous basic solution at a temperature greater than about 25° C.

Zeolites, such as mordenite are known to catalyse hydrocarbon conversion reactions such as cracking and hydrocracking. For example, in U.S. Pat. No. 3,374,182 there is described a method for treating mordenites with aqueous caustic solutions for use in hydrocatalytic conversion reactions. Similarly, DE 41 16 630 describes a method for the insertion of elements into crystalline aluminosilicates which may be used to catalyse hydrocarbon conversion reactions.

Carbonylation processes for the production of acetic acid and/or methyl acetate by carbonylating methanol and/or reactive derivatives thereof with carbon monoxide are known. Such processes typically employ Group VIII metal catalysts, such as rhodium and iridium. Mordenites are also known to catalyse carbonylation reactions. For example, there is described in EP-A-1 985 362 a process for the carbonylation of dimethyl ether in the presence of a mordenite catalyst. In EP-A-1 985 362 it was found that improved catalytic activity could be achieved by using a mordenite catalyst which had been loaded with silver and/or copper and also a low level of platinum.

Thus, it is known to improve the carbonylation catalytic activity of mordenite by employing promoter metals. However, the use of expensive metals is not desirable and thus there is a need to find alternative methods of improving the catalytic activity of mordenite in carbonylation processes, and, in particular, to improve the catalytic activity of mordenite in the carbonylation of methanol and/or reactive derivatives thereof to produce acetic acid and/or methyl acetate.

It has now been found that the catalytic activity of mordenite in carbonylation reactions can be improved by subjecting the mordenite to a treatment with an aqueous basic solution containing at least one of aluminate ions and gallate ions.

Accordingly, the present invention provides a process for the production of at least one carbonylation product selected from acetic acid and methyl acetate which process comprises carbonylating at least one carbonylatable reactant selected from methanol and reactive derivatives thereof with carbon monoxide in the presence of a catalyst, wherein said catalyst is a mordenite which has been treated with an aqueous basic solution containing at least one of aluminate ions and gallate ions and has a silica:$X_2O_3$ ratio (wherein X is Al and/or Ga) of at least 12:1.

The mordenite for use as catalyst in the carbonylation process of the present invention is a mordenite which has been subjected to a treatment with an aqueous basic solution containing one or more of aluminate ions and gallate ions.

The structure of mordenite is defined, for example, in The Atlas of Zeolite Framework Types (C. Baerlocher, W. M. Meier, D. H. Olson, 5$^{th}$ ed. Elsevier, Amsterdam, 2001). The web-based version (http://www.iza-structure.org/databases/) is a compendium of topological and structural details about zeolites including mordenite.

Mordenite is a naturally occurring zeolite but can be synthesised and obtained commercially. Commercially available forms of mordenite include the sodium form, the acid form and the ammonium form. The mordenite to be treated may be any form of mordenite, but is preferably the H-form (acid form) or the ammonium form of mordenite.

It has been found that treating mordenites with an aqueous basic solution containing aluminate and/or gallate ions decreases the silica:$X_2O_3$ (where X is Al and/or Ga) molar ratio of mordenites. Advantageously, this decrease in the silica:$X_2O_3$ ratio has been found to result in mordenites having significantly superior carbonylation catalytic activity compared to equivalent but untreated mordenites. It has also been found that the carbonylation catalytic activity of the treated mordenites is superior to mordenites which have been treated with an aqueous basic solution in the absence of aluminate and gallate ions.

The mordenite to be treated with the aqueous basic solution containing aluminate and/or gallate ions may have a silica:alumina ratio of at least 12:1, suitably in the range 12 to 250:1, for example, in the range 20 to 100:1, such as in the range 25 to 60:1.

The aqueous basic solution employed herein is preferably composed of an alkali metal hydroxide, such as sodium hydroxide or ammonium hydroxide, dissolved in water. However, other alkaline alkali metal salt solutions may be employed, such as sodium carbonate solutions provided that the pH is greater than 8.

The aqueous basic solution may be generated by dissolving a sufficient concentration of a suitable base in water to provide a pH of greater than 8. Typically, the pH of the solution is 11 or above, preferably, in the range 11 to 14.

Suitable concentrations of alkali metal hydroxide/ammonium hydroxide solutions, such as sodium hydroxide solution are in the range 0.01 M to 1.0 M.

The mordenite is also treated with at least one of aluminate and gallate ions. By 'aluminate ions' is meant the monomeric ionic species, $Al(OH)_4^-$ and by 'gallate ions' is meant the monomeric ionic species, $Ga(OH)_4^-$.

The generation of aluminate and gallate ions is known. Any suitable source of aluminium and gallium which is soluble in the chosen aqueous basic solution and which generates aluminate and gallate ions respectively therein may be used. Suitable sources include aluminium and gallium metals, aluminium-containing compounds and gallium-containing compounds Suitably, aluminate ions may be formed, for example, by dissolving aluminium metal and/or aluminium-containing compounds in an excess of an aqueous solution of a base.

Suitable aluminium-containing compounds include alkali metal aluminates, such as sodium aluminate and aluminium salts such as aluminium sulphate, aluminium nitrate, aluminium hydroxide and aluminium acetate.

Gallate ions may be formed, for example, by dissolving gallium metal and/or gallium-containing compounds in an excess of an aqueous solution of a base.

Suitable gallium-containing compounds which may be used include gallium acetylacetonate, gallium acetate, gallium nitrate and gallium hydroxide.

Preferably, the mordenite is treated with an aqueous basic solution containing gallate ions.

The mordenite may be treated in a single step procedure or in a multiple step procedure.

In a single step procedure, mordenite may be treated with a single aqueous solution of a base containing aluminate and/or gallate ions. Such a solution can be obtained by generating aluminate and/or gallate ions in-situ in an aqueous solution of a base. Alkali metal hydroxides, such as sodium hydroxide, or ammonium hydroxide may serve as the base. For example, a single solution may be obtained by the addition of an aqueous solution of an aluminium and/or gallium containing compound to an aqueous solution of a base such as sodium hydroxide or ammonium hydroxide.

Alternatively, the mordenite may be treated in a multiple step operation wherein the mordenite is treated sequentially with separate aqueous solutions of (a) a base and (b) aluminate and/or gallate ions or a source thereof. Suitably, the mordenite is contacted in a first step with an excess of an aqueous solution of a base and in a second step with an aqueous solution of an aluminium and/or gallium containing compound.

Where mordenite is treated sequentially, the aqueous solution containing aluminate and/or gallate ions or a source thereof, the solution may be added in a continuous manner to the base treated mordenite or it may be added as a single dosage.

The concentration of aluminate and/or gallate ions in the aqueous basic solution may be varied depending on the desired treatment level. It has been found that an effective concentration of aluminate ions in the aqueous basic solution can be generated from aluminium in an amount in the range 0.05 mmol aluminium per gram of mordenite to 2 mmol of aluminium per gram of mordenite.

An effective concentration concentration of gallate ions in the aqueous basic solution can be generated from gallium in an amount in the range 0.05 mmol gallium per gram of mordenite to 2 mmol of gallium per gram of mordenite.

The temperature and duration for which the treatment is carried out is not critical. However, for any given desired treatment level, the duration of the treatment will depend upon the temperature employed, the concentration of the base and the concentration of aluminate or gallate ions and the physical and chemical characteristics of the mordenite precursor, and, in particular, the silica:alumina ratio. Typically, a duration of at least 30 minutes up to several hours may be employed.

Typically, temperatures in the range 60 to 100° C. may be employed. Lower temperatures may be employed, for example, temperatures of 50° C. and below but, in general, the lower the temperature employed, the greater the duration of the treatment that is required to obtain a desired treatment level.

It has been found that an effective treatment may be carried out by treating a mordenite of silica:alumina molar ratio in the range 25 to 60:1, such as 30 to 50:1, with a source of aluminate and/or gallate ions dissolved in an excess of an aqueous alkali metal hydroxide, such as sodium hydroxide, the alkali metal hydroxide solution preferably having a pH in the range 11 to 14, at a temperature in the range 50 to 100° C., preferably, 60 to 80° C. for at least 30 minutes, such as for a duration of 0.5 to 24 hours, preferably, 0.5 to 10 hours.

Suitably, the silica:$X_2O_3$ ratio of the treated mordenite is at least 12:1, suitably in the range 12 to 250:1, for example, in the range 20 to 100:1 or 20 to 250:1, such as 25 to 60:1 and 20 to 40:1.

Typically, the treated mordenite will have a greater mesopore volume than that of the pre-treated mordenite. It has been found that the addition of aluminate and/or gallate ions to an aqueous base solution results in little or no change to the mesopore volume of a mordenite which has been treated with an aqueous solution of base. Thus, the increase in mesopore volume in mordenites treated with an aqueous basic solution containing aluminate and/or gallate ions is believed to be largely due to the effect of the base.

Suitably, the treated mordenites have a mesopore volume in the range 0.10 and 0.50 ml/g.

Preferably, the treated mordenites have a silica:$X_2O_3$ ratio in the range 25 to 60:1 and a mesopore volume in the range 0.10 to 0.50 ml/g.

Following treatment with the aqueous basic solution containing aluminate and/or gallate ions, the mordenite is filtered off and washed with water to remove any excess base and metal species and then dried. The resulting treated mordenite may be used as such as the catalyst in the carbonylation process of the present invention or it may be converted to the H-form of the mordenite.

Treatment of a hydrogen or ammonium form of mordenite with an aqueous solution of an alkali metal hydroxide will result in exchange of the hydrogen or ammonium ions with alkali metals ions. However, for use as catalyst in the carbonylation process of the present invention, it is preferred that the mordenite is in the ammonium form and more preferably, is in the H-form. Thus, as is well-known in the art, the alkali metal form can be converted to the ammonium form by exchanging it with aqueous solutions of ammonium salts.

The ammonium form of mordenite may be converted to the H-form by a heat treatment, such as calcination, to effect thermal decomposition of the ammonium ions and formation of the H-form of the mordenite. Calcination may be carried out at a temperature of at least 400° C., such as in the range 400 to 600° C., for example 450 to 550° C.

In a typical treatment, a source of aluminium and/or gallium is dissolved in an excess of an aqueous solution of a base, such as sodium hydroxide. A H-mordenite of silica:$X_2O_3$ ratio in the range 25 to 60:1 is added to the solution and heated at a temperature of 65° C. for at least 30 minutes. Subsequently, the reaction is quenched and cooled, for example, by submersion of the vessel in an ice-water mixture, followed by filtration and washing with deionised water. After filtration and washing, the mordenite is dried. Drying is typically carried out at about 110° C. The treated mordenite may be converted to the $NH_4$-form of the mordenite by three successive exchanges with an ammonium nitrate solution. The exchanged mordenite is then dried, typically at 110° C. and calcined. Calcination may be carried out in static air at a temperature sufficient to convert the ammonium form to the H-form of the mordenite, such as at a temperature in the range 450 to 550° C.

The treated mordenites of the present invention are useful as catalysts in carbonylation processes, for example in the carbonylation of carbonylatable reactants such as methanol and/or reactive derivatives thereof.

Thus, the present invention further provides for the use of a catalyst which is a mordenite of silica:$X_2O_3$ ratio of at least 12:1 which mordenite has been treated with an aqueous basic solution containing at least one of aluminate and gallate ions to provide improved catalytic activity in a process for the production of at least one carbonylation product selected from acetic acid and methyl acetate which process comprises carbonylating at least one carbonylatable reactant selected from methanol and reactive derivatives thereof with carbon monoxide.

The catalyst may be employed in the carbonylation process of the present invention in any suitable form such as powders, pellets or other forms of extrudates.

The catalyst may be combined with a binder material. Any suitable binders may be employed. Particularly useful binders are inorganic oxide materials such as one or more of the group selected from silica, alumina, silica-alumina, magnesium silicate and magnesium aluminium silicate, preferably, alumina or silica-alumina. Examples of suitable aluminas include boehmite type alumina and gamma-alumina.

Preferably, a binder is a refractory inorganic oxide such that the inorganic oxide is stable at high temperature, and, in particular is stable at temperatures which may be employed in calcination of the catalyst, such as a temperature of at least 400° C., for example, a temperature in the range 400 to 550° C.

Suitable binders may be mesoporous, for example inorganic oxides having a mesoporosity in the range 1 to 500 $m^2/g$. By mesoporosity is meant the sum of the total surface area of mesopores and the external surface area of the binder as measured by nitrogen BET. A mesopore is a pore having a diameter in the range 2 to 50 nanometers.

Preferably, mesoporous binders will also have low microporosity, such as a microporosity in the range 1 to 100 $m^2/g$, preferably in the range 1 to 10 $m^2/g$. By microporosity is meant the sum of the total surface area of micropores and the external surface area of the binder as measured by nitrogen BET. A micropore is a pore having a diameter of less than 2 nanometers.

Suitably, a binder may be present in an amount in the range of 10% to 80% by weight of the catalyst, preferably, in the range of 20% to 65% by weight of the catalyst, and, more preferably, in an amount in the range 35 to 65% by weight of the catalyst.

Suitably, the catalysts for use in the carbonylation process of the present invention may be combined with a binder which is a refractory inorganic oxide selected from one or more of silica, alumina and silica-alumina, which inorganic oxide is mesoporous, and preferably, an inorganic oxide having a mesoporosity in the range 50 to 500 m2/g.

In the carbonylation process of the present invention methanol and/or a reactive derivative thereof is carbonylated with carbon monoxide. Reactive derivatives of methanol which may be used as an alternative to, or in addition to methanol, include methyl acetate and dimethyl ether. A mixture of methanol and a reactive derivative thereof, for example a mixture of methanol and methyl acetate, may be employed. Where dimethyl ether is the carbonylatable reactant, it may be generated in-situ from a suitable source, such as dimethyl carbonate. For example, liquid dimethyl carbonate may be contacted with gamma-alumina to decompose the dimethyl carbonate to dimethyl ether and carbon dioxide.

Depending on the nature of the carbonylatable reactant used, the process may be carried out under hydrous or substantially anhydrous conditions. Preferably, where methyl acetate is used as the carbonylatable reactant, the process is carried out in the presence of water. Water may be present in the feed at a molar ratio of methyl acetate:water in the range 50:1 to 2:1. Where the carbonylatable reactant is dimethyl ether, water has been found to inhibit the carbonylation process, thus it is preferred that when using these reactants, the process is carried out under substantially anhydrous conditions. By 'substantially anhydrous' is meant that, in the process, water is kept as low as is feasible. To accomplish this, the dimethyl ether and carbon monoxide reactants (and catalyst) are preferably dried prior to introduction into the process. However, small amounts of water may be tolerated without adversely affecting the formation of methyl acetate product. Suitably, water may be present in the carbonylatable reactant gaseous feed(s) to the reactor in an amount of less than 2.5 wt %, for example, less than 0.5 wt % relative to the amount of dimethyl ether.

The purity of the carbon monoxide used is not deemed to be especially critical although it is desirable to use gas mixtures in which carbon monoxide is the main component. The presence of small amounts of impurities such as nitrogen and the noble gases can be tolerated. The carbon monoxide may be used in admixture with hydrogen. Suitably, the ratio of $CO:H_2$ is in the range 1:3 to 15:1 on a molar basis, such as 1:1 to 10:1. For example, mixtures of carbon monoxide and hydrogen as produced by the reforming or partial oxidation of hydrocarbons (synthesis gas) may also be used in the process of the present invention.

The carbonylation process of the present invention is preferably carried out by passing methanol vapour and/or dimethyl ether vapour and carbon monoxide gas, optionally in the presence of hydrogen, through a fixed or fluidised bed of the catalyst maintained at the desired temperature and pressure.

The carbonylation process may suitably be carried out at a temperature in the range of 100° C. to 400° C., such as 150 to 350° C.

The carbonylation process may be carried out at a pressure in the range 1 to 100 barg, such as 10 to 100 barg.

The molar ratio of carbon monoxide to carbonylatable reactant is suitably in the range 1:1 to 99:1, such as 1:1 to 60:1.

Hydrogen may be present in the carbonylation process, and may be present at a partial pressure of at least 0.1 barg, such as 1 to 30 barg.

The Gas Hourly Space Velocity (GHSV) is suitably in the range 500 to 40,000 $h^{-1}$, such as 2000 to 10,000 $h^{-1}$.

Prior to use in the carbonylation process, the catalyst is activated by, for example, by subjecting the catalyst to elevated temperature for at least one hour under flowing nitrogen, carbon monoxide or hydrogen.

If desired, the carbonylatable reactant may be contacted with a bed of alumina or corundum immediately before the bed of catalyst.

Preferably, the process of the present invention is carried out substantially in the absence of halides, such as iodide. By substantially is meant that the halide content, such as the iodide content of the feed gases and catalyst are less than 500 ppm and preferably less than 100 ppm.

The process may be carried out either as a fixed bed, fluid bed or moving bed process.

The process may be operated as either a continuous or a batch process, preferably as a continuous process.

The product of the carbonylation process is acetic acid and/or methyl acetate. Where the carbonylatable reactant is methanol, the carbonylation product is acetic acid but methyl acetate may also be produced, depending on the extent of carbonylation.

Where the carbonylatable reactant is dimethyl ether the primary product of the process is methyl acetate but small amounts of acetic acid may also be produced.

The acetic acid produced by the process of the present invention can be removed in the form of a vapour and thereafter condensed to a liquid. The acetic acid can be subsequently purified using conventional techniques, such as distillation.

Where methyl acetate is a product of the process, at least some may be recovered from the carbonylation reaction products and sold as such and/or recycled to the carbonylation reactor and/or at least a portion may be recovered and used as such as a feedstock for other chemical processes, and/or at least a portion of it may be hydrolysed to acetic acid using known techniques, such as reactive distillation in the presence of an acid catalyst.

The invention will now be illustrated with reference to the following Examples.

EXAMPLE 1

Catalyst Preparation
(i) Catalyst A: H-Mordenite Treated with Sodium Hydroxide and Sodium Aluminate 0.082 g of $NaAlO_2$ was dissolved in an aqueous basic solution (300 ml of aqueous NaOH 0.2M). The solution was heated to 65° C. with vigorous stirring. After the system had reached equilibrium, 10 g of mordenite (H-mordenite of silica:alumina ratio of 40 ex BASF) was added and stirred continuously for 30 minutes after which the suspension was cooled in ice cold water under stirring. The mixture was then filtered under vacuum, washed with 1 liter deionised water and dried overnight at 110° C. in air. The mordenite was exchanged 3 times with an aqueous solution of $NH_4NO_3$ (10 ml/g of zeolite, 1M) at 80° C. for a period of 1 hour. Following each exchange step the $NH_4$-mordenite was washed with deionised water. The wet $NH_4$-mordenite was dried at 110° C. and then converted to the H-form of the mordenite by calcining in air at 500° C. for 5 hours.
(ii) Catalyst B: H-Mordenite Treated with Sodium Hydroxide Catalyst B was prepared by repeating the preparation of Catalyst A except that no $NaAlO_2$ was added to the aqueous basic solution.
(iii) Catalyst C The H-mordenite precursor used to prepare Catalysts A and B above was used as Catalyst C.

Characterisation

Certain physiochemical properties of Catalysts A, B and C are given in Table 1.

TABLE 1

|  | $V_{mesopores}$ (ml/g) | $S_{external}$ (m$^2$/g) | Silica:Alumina molar ratio |
|---|---|---|---|
| Catalyst A (H-MOR $NaAlO_2$/NaOH) | 0.41 | 151 | 25 |
| Catalyst B (H-MOR NaOH) | 0.44 | 121 | 28.6 |

TABLE 1-continued

|  | $V_{mesopores}$ (ml/g) | $S_{external}$ (m$^2$/g) | Silica:Alumina molar ratio |
|---|---|---|---|
| Catalyst C (H-MOR) | 0.1 | 50 | 40.5 |

The properties of the three mordenites were determined using the following analytical techniques. $N_2$ adsorption was carried out at 77K in a Micromeritics Tristar 3000 apparatus equipped with Tristar 3000 v6.01 software for data analysis. Before the analysis, samples were degassed under vacuum at 60° C. for 30 minutes and then at 120° C. for 16 hours. The T-plot method was used to determine the external surface area using a fitted thickness range of 0.35-0.5 nm [B. C. Lippens, J. H. de Boer, J. Catal. 4 (1965) 319]. The mesopore volume was calculated by substracting the micropore volume from the total pore volume (determined using the single point adsorption total pore volume; $p/p_0 > 0.98$).

The silica:alumina molar ratio was determined by inductively coupled plasma atomic emission spectrometry (ICP-OES).

Carbonylation Reactions Using Catalysts A, B and C

Prior to use 0.75 g of each catalyst was compacted at 12 tonnes in a 33 mm die set using a pneumatic press, and crushed and sieved to a particle size fraction of 250 to 500 microns. A Hastelloy reactor tube was packed with 0.6 ml catalyst and 0.2 g of a pre-bed of gamma alumina. The portion of the reactor tube containing the catalyst was heated by means of an electrical heating jacket. The reactor and heating jacket were themselves mounted in a heated cabinet which maintained the temperature of the pre-bed. The heated cabinet was typically maintained at 130° C. Prior to start-up of the carbonylation reaction, the reactor was heated at atmospheric pressure to 130° C. under a flow of nitrogen. Once at 130° C., a gas comprising 80 mole % carbon monoxide and 20 mole % hydrogen was introduced into the reactor at a flow rate (GHSV) of 5000 per hour, and the reactor pressurised to 20 barg, heated to a temperature of 300° C. and maintained under these conditions for 2 hours. The carbonylation reaction was then started by feeding liquid dimethyl carbonate at a rate designed to give a gas feed comprising 76 mole % carbon monoxide, 19 mole % hydrogen and 5 mole % dimethyl ether. The reaction was allowed to continue for 100 hours under conditions of 300° C., 20 bar, and a gas hourly space velocity (GHSV) of 5000 h$^{-1}$. A constant flow of reaction off-gases was taken, let down to atmospheric pressure at a temperature of 130° C. and passed to a gas chromatograph for analysis of acetyls products (acetic acid and methyl acetate). The results of the carbonylation reactions are shown in Tables 2 and 3.

TABLE 2

Space Time Yield vs. Time on Stream (TOS)

| | Acetyls STY (g/l/hr) | | |
|---|---|---|---|
| Catalyst | TOS = 10 h | TOS = 20 h | TOS = 40 h |
| Catalyst A | 252 | 236 | 228 |
| Catalyst B | 165 | 140 | 138 |
| Catalyst C | 63 | 47 | 39 |

The data in Table 2 clearly shows that Catalyst A (treated with an aqueous basic solution containing aluminate ions) is more effective than Catalyst B (treated with base only) and Catalyst C (H-mordenite untreated), in converting dimethyl ether to the carbonylation products, methyl acetate and acetic acid.

TABLE 3

Turn Over Frequency vs. Time on Stream

| Catalyst | TOF* (mol/mol/hr) | | |
|---|---|---|---|
| | TOS = 10 h | TOS = 20 h | TOS = 40 h |
| Catalyst A | 9.0 | 8.4 | 8.1 |
| Catalyst B | 6.0 | 5.1 | 5.0 |
| Catalyst C | 3.3 | 2.4 | 2.0 |

*TOF: moles of acetyls created per mole of Al per hour.

The results in Table 3 clearly show that the active sites of Catalyst A are more effective than those of either Catalyst B or Catalyst C.

EXAMPLE 2

Catalyst Preparation
Catalyst D: H-Mordenite Treated with Sodium Hydroxide and Sodium Aluminate and Combined with a Binder.

Catalyst D was prepared by combining a treated mordenite in the ammonium form with a binder. The treated mordenite in the ammonium form was prepared by repeating the preparation method of Catalyst A except that (i) the ammonium exchanged mordenite was not calcined after drying and (ii) the amounts used were 0.41 g of NaAlO2 dissolved in 1.5 L of aqueous NaOH (0.2M), 50 g of mordenite (H-mordenite of silica:alumina ratio of 40 ex BASF) and the washing of the filtered mordenite was conducted using 5 liters deionised water prior to drying at 110° C.

30 g of the treated mordenite and 15 g of an alumina binder (ex Sasol, Pural SCF) were combined by gently milled together in a Büchi powder drying flask until a free flowing powder was produced. The powder was blended on a rotor evaporator with a speed of 100 r.p.m. for 1 hour at ambient temperature and pressure and then calcined for 3 hours at 500° C. under an atmosphere of static air.

Catalyst E: H-Mordenite Combined with a Binder
30 g of H-mordenite (of silica:alumina ratio of 40 ex BASF) and 15 g of binder (ex Sasol, Pural SCF) were combined by repeating the method as used in the preparation of Catalyst D above.

Carbonylation Reactions Using Catalysts D and E
Carbonylation reactions of dimethyl ether with carbon monoxide were performed using Catalyst D and Catalyst E.

Prior to loading in a reactor each catalyst was compacted at 10 tonnes in a 13 mm die set using a pneumatic press, and crushed and sieved to a particle size fraction of 125 to 160 microns.

The carbonylation reactions were carried out in a pressure flow reactor unit consisting of 16 identical reactors of the type described in WO 2005063372. Each reactor had an internal diameter of 9.2 mm and the centre of each reactor was fitted with a tube of diameter 3.2 mm into which a thermocouple was placed.

A 10 cm corundum bed of sieve fraction of 125-160 µm was placed in each reactor. On a dry mass basis (determined by loss on ignition of the catalyst measured by heating the catalyst from room temperature to 600° C. at a ramp rate of 30° C. per minute), 1.948 g (approximately 3 ml) of a catalyst diluted with 3 ml of corundum was placed on top of the corundum bed. The diluted catalyst was covered by 11 cm bed of corundum of particle size of 125-160 microns. 1 g of gamma-alumina (ex BASF SAS 250) of pellet size 125-160 microns was placed on top of the corundum, to a depth of 2 cm.

The reactors were pressurised to a reaction pressure of 70 bar with a gas feed of a 4:1 molar ratio of carbon monoxide: hydrogen at a flow rate of 12 L/h per reactor. The reactors were then heated at 1° C./min to a holding temperature of 220° C., where they were held for a dwell time of 3 hours. The temperature was then ramped to 300° C. at 1° C./min, again followed by a dwell time of 3 hours. The gas feed was then changed to a mixture of carbon monoxide, hydrogen, dimethyl ether, argon and methyl acetate at a molar ratio of 70.8:17.7:6:5:0.5 respectively at a total flow rate of 12 L/h per reactor, with a dimethyl ether vapour feed rate of 0.72 L/h per reactor and a methyl acetate vapour feed rate of 0.06 L/h per reactor. Nitrogen was introduced at a variable rate of 0-150 ml/min to equalise the pressure swings between the 16 reactor exits. The exit stream from each reactor was periodically passed to a gas chromatograph to determine the concentration of reactants and carbonylation products. The reaction was allowed to continue for 263 hours under conditions of 300° C., 70 bar and a gas hourly space velocity (GHSV) of 4000/h.

From the gas chromatography analysis, the space time yield (STY) of acetyls products was calculated as the molar equivalent weight of acetic acid corresponding to the sum of the methyl acetate and acetic acid produced expressed as grams of acetic acid per hour per liter of catalyst. The acetyls product was predominantly methyl acetate. The results are given in Table 4.

TABLE 4

Space Time Yield vs. Time on Stream (TOS)

| Catalyst | Acetyls STY (g/l/hr) | | |
|---|---|---|---|
| | TOS = 50 h | TOS = 100 h | TOS = 140 h |
| Catalyst D | 323 | 317 | 317 |
| Catalyst E | 195 | 153 | 133 |

TOS = time on stream

The results in Table 4 clearly show Catalyst D (treated mordenite combined with a binder) is more effective than the parent catalyst, Catalyst E (untreated mordenite combined with a binder).

EXAMPLE 3

Catalyst Preparation
Catalyst F: H-Mordenite Treated with Sodium Hydroxide and Gallium Nitrate and Combined with a Binder 10 g of H form mordenite (silica:alumina ratio of 230 ex Tosoh) was treated with an aqueous solution of NaOH (0.2M, 300 ml) for 1 h at 35° C. An aqueous solution of gallium nitrate (1 mmol of $Ga(NO_3)_3$ dissolved in 50 ml water) was then added and the mixture was stirred at 35° C. for 1 h. The solution was filtered under vacuum, washed with 1 liter deionised water and dried overnight at 110° C. in air. The dried mordenite was exchanged 3 times with an aqueous solution of $NH_4NO_3$ (10 ml/g of zeolite, 1M) at 80° C. for a period of 1 hour. Following each exchange step the $NH_4$-mordenite was washed with deionised water. The wet $NH_4$-mordenite was dried at 110° C. and then converted to the H-form of the mordenite by calcining in air at 500° C. for 5 hours.

4 g of the calcined mordenite and 4 g of an alumina binder (ex Sasol, Pural SCF) were gently milled together in a Büchi powder drying flask until a free flowing powder was produced. The powder was blended on a rotor evaporator with a speed of 100 r.p.m. for 1 hour at ambient temperature and pressure and then calcined for 3 hours at 500° C. under an atmosphere of static air.

Catalyst G: H-Mordenite Treated with Sodium Hydroxide and Sodium Aluminate and Combined with a Binder Catalyst G was prepared by repeating the method of Catalyst F except that the gallium nitrate was replaced by sodium aluminate (1 mmol of $NaAlO_2$ dissolved in 50 ml water).

Catalyst H: H-Mordenite Combined with Alumina Binder 10 g of H form mordenite (ex Tosoh; silica:alumina ratio of 230:1) and 10 g of alumina binder (ex Sasol, Pural SCF) were combined using the method as described in the preparation of Catalyst F.

Carbonylation Reactions Using Catalysts F, G and H

The carbonylation reactions were carried out in a pressure flow reactor unit consisting of 16 identical parallel isothermal co-current tubular reactors of the type described in, for example, WO2006107187. The reactors were arranged in 4 blocks of 4 reactors, each block having an independent temperature control. Each reactor had a metal sinter of pore size 20 micrometers onto which was placed 0.072 g of a catalyst pressed and sieved to 100-160 μm (approximately 100 μL) to give a gas hourly space velocity (GHSV) of 4000 $h^{-1}$. Carborundum was placed on top of the catalyst bed. Each catalyst was heated at atmospheric pressure to 300° C. at a ramp rate of 5° C./min. under nitrogen at a flow rate of 3.1 mL/min. per reactor and held at 300° C. for 1 hour. Nitrogen was then replaced by a gaseous feed of 77.6 mole % carbon monoxide, 19.3 mole % hydrogen and 3.1 mole % He at a flow rate of 6.1 ml/min. per reactor. The pressure was then raised to 60 barg and left to equilibrate for two hours. A gas feed comprising 69.7 mol % carbon monoxide, 17.5 mol % hydrogen, 2.8 mol % He and 10 mol % dimethyl ether was introduced into each reactor at a flow rate of 6.7 ml/min. per reactor. The reaction was continued for 120 hours. The exit stream from each reactor was periodically passed to a gas chromatograph to determine the concentration of reactants and carbonylation products.

From the gas chromatography analysis, the space time yield (STY) of acetyls products was calculated as the molar equivalent weight of acetic acid corresponding to the sum of the methyl acetate and acetic acid produced expressed as grams of acetic acid per hour per liter of catalyst. The acetyls product was predominantly methyl acetate. The results are given in Table 5.

TABLE 5

| | Acetyls STY (g/l/hr) | | |
|---|---|---|---|
| Catalyst | TOS = 20 h | TOS = 60 h | TOS = 110 h |
| Catalyst F | 227 | 233 | 215 |
| Catalyst G | 96 | 84 | 75 |
| Catalyst H | 41 | 27 | 22 |

TOS = time on stream

The results in Table 5 clearly show that Catalyst F (mordenite treated with an aqueous basic solution containing gallate ions) and Catalyst G (mordenite treated with an aqueous basic solution containing aluminate ions) have significantly improved carbonylation catalytic activity than Catalyst H (untreated mordenite).

The invention claimed is:

1. A process for the production of at least one carbonylation product selected from acetic acid and methyl acetate which process comprises carbonylating at least one carbonylatable reactant selected from methanol and reactive derivatives thereof with carbon monoxide in the presence of a catalyst, wherein said catalyst is a mordenite which has been treated with an aqueous basic solution containing at least one of aluminate ions and gallate ions and has a silica: $X_2O_3$ molar ratio wherein X is Al and/or Ga of at least 12:1.

2. A process according to claim 1 wherein the mordenite has a silica:$X_2O_3$ molar ratio in the range 12 to 250:1.

3. A process according to claim 1 wherein the aqueous basic solution has a pH in the range 11 to 14.

4. A process according to claim 1 wherein the aqueous basic solution is an aqueous solution of sodium hydroxide or ammonium hydroxide.

5. A process according to claim 1 wherein the mordenite has been treated in a single step or a multiple step procedure.

6. A process according to claim 5 wherein the single step procedure comprises treating the mordenite with a single aqueous basic solution containing at least one of aluminate and gallate ions obtained by generating the aluminate and/or gallate ions in-situ in an aqueous solution of a base.

7. A process according to claim 5 wherein the multiple step procedure comprises treating the mordenite sequentially with separate aqueous solutions of (a) base and (b) aluminate and/or gallate ions or a source thereof.

8. A process according to claim 1 wherein the mordenite has been treated with an aqueous basic solution containing gallate ions.

9. A process according to claim 1 wherein the catalyst is H-mordenite.

10. A process according to claim 1 wherein the catalyst is combined with a binder which is a refractory inorganic oxide selected from the group consisting of at least one of silica, alumina, silica-alumina, magnesium silicate and magnesium aluminium silicate.

11. A process according to claim 1 wherein the carbonylatable reactant is a reactive derivative which is dimethyl ether.

12. A process according to claim 11 wherein water is present in the carbonylatable reactant in an amount of less than 2.5 wt % relative to the amount of dimethyl ether.

13. A process according to claim 1 wherein the process is carried out in the presence of hydrogen.

14. A process according to claim 1 wherein the carbonylation product is methyl acetate and at least a portion of the methyl acetate is hydrolysed to acetic acid.

* * * * *